(12) United States Patent
Arcilla et al.

(10) Patent No.: US 10,589,053 B2
(45) Date of Patent: *Mar. 17, 2020

(54) ACTIVE VALVE FOR VENTILATORS

(71) Applicant: KONINKLIJKE PHILIPS N.V., Eindhoven (NL)

(72) Inventors: Mabini Arcilla, Carlsbad, CA (US); Samir Ahmad, San Diego, CA (US); Eamonn Kelly, Carlsbad, CA (US)

(73) Assignee: Koninklijke Philips N.V., Eindhoven (NL)

( * ) Notice: Subject to any disclaimer, the term of this patent is extended or adjusted under 35 U.S.C. 154(b) by 185 days.

This patent is subject to a terminal disclaimer.

(21) Appl. No.: 15/492,019

(22) Filed: Apr. 20, 2017

(65) Prior Publication Data

US 2017/0216553 A1 Aug. 3, 2017

Related U.S. Application Data

(62) Division of application No. 13/994,847, filed as application No. PCT/IB2011/055574 on Dec. 9, 2011, now Pat. No. 9,656,040.

(60) Provisional application No. 61/425,515, filed on Dec. 21, 2010.

(51) Int. Cl.
| | |
|---|---|
| *A61M 11/00* | (2006.01) |
| *A61M 16/20* | (2006.01) |
| *A62B 9/02* | (2006.01) |
| *F16K 31/08* | (2006.01) |
| *A61M 16/00* | (2006.01) |

(52) U.S. Cl.
CPC .......... *A61M 16/204* (2014.02); *A61M 16/20* (2013.01); *A61M 16/206* (2014.02); *A61M 16/209* (2014.02); *A62B 9/02* (2013.01); *F16K 31/08* (2013.01); *F16K 31/082* (2013.01); *A61M 2016/0021* (2013.01); *A61M 2016/0027* (2013.01); *A61M 2205/52* (2013.01); *Y10T 137/0379* (2015.04); *Y10T 137/86485* (2015.04)

(58) Field of Classification Search
None
See application file for complete search history.

(56) References Cited

U.S. PATENT DOCUMENTS

| | | | |
|---|---|---|---|
| 3,976,064 A | * | 8/1976 | Wood .................. A61M 16/022 128/204.21 |
| 4,502,481 A | | 3/1985 | Christian |
| 4,579,145 A | | 4/1986 | Leiber et al. |
| 4,951,661 A | | 8/1990 | Sladek |
| 5,127,400 A | | 7/1992 | DeVries et al. |
| 5,265,594 A | | 11/1993 | Olsson |

(Continued)

FOREIGN PATENT DOCUMENTS

| | | |
|---|---|---|
| CN | 1623608 A | 6/2005 |
| CN | 101310792 A | 11/2008 |

(Continued)

*Primary Examiner* — Daniel J Colilla
(74) *Attorney, Agent, or Firm* — Michael W. Haas

(57) ABSTRACT

A method for controlling a ventilator includes the steps of providing an inhalation pressure limit, determining when a pressure in a connection to a patient circuit is greater than the inhalation pressure limit, and opening the valve when the pressure is greater than the inhalation pressure limit. An associated computer readable medium for controlling the method is also described.

8 Claims, 3 Drawing Sheets

(56) References Cited

U.S. PATENT DOCUMENTS

| | | | |
|---|---|---|---|
| 5,596,984 A * | 1/1997 | O'Mahony | A61M 16/20 128/204.18 |
| 5,694,926 A | 12/1997 | DeVries et al. | |
| 5,791,339 A | 8/1998 | Winter | |
| 6,095,496 A | 8/2000 | Rydin et al. | |
| 7,152,597 B2 | 12/2006 | Bathe | |
| 7,815,166 B2 | 10/2010 | Hoffman et al. | |
| 2004/0069305 A1 | 4/2004 | Niemela | |
| 2008/0078389 A1 * | 4/2008 | Xiao | A61M 16/12 128/204.22 |
| 2010/0224191 A1 | 9/2010 | Dixon et al. | |

FOREIGN PATENT DOCUMENTS

| | | | |
|---|---|---|---|
| CN | 101856354 A | 10/2010 | |
| DE | 102008017339 A1 * | 10/2009 | A61M 16/00 |
| JP | 6212348 U | 1/1987 | |
| JP | H04200478 A | 7/1992 | |
| JP | 10179742 A * | 7/1998 | |
| JP | 200014784 A | 1/2000 | |
| WO | 199531241 A1 | 11/1995 | |
| WO | 2009006932 A1 | 1/2009 | |
| WO | 2010101778 A1 | 9/2010 | |
| WO | 2010141983 A1 | 12/2010 | |

\* cited by examiner

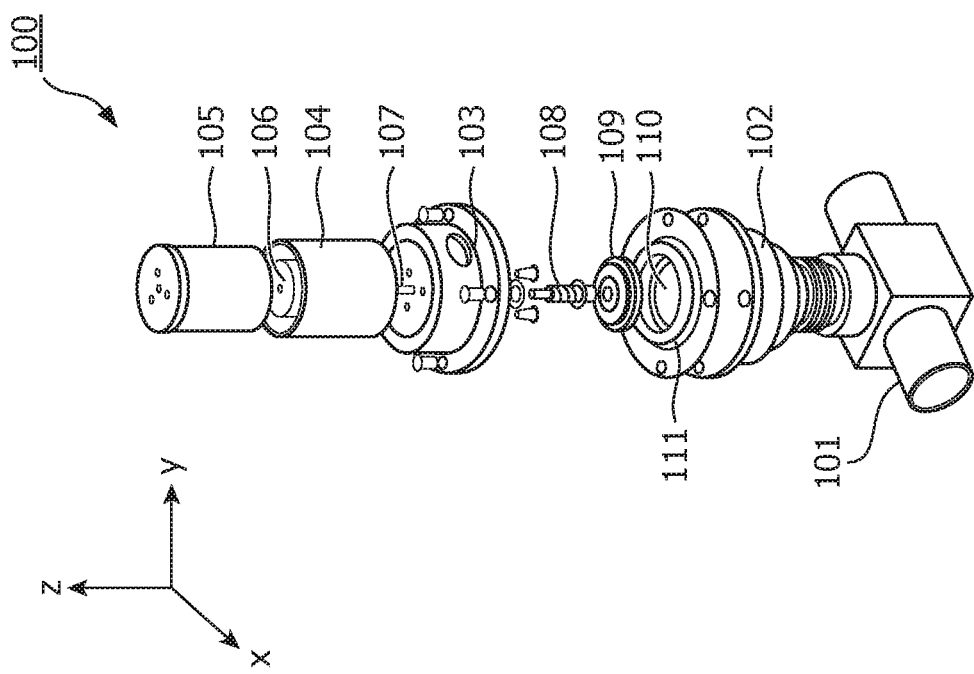
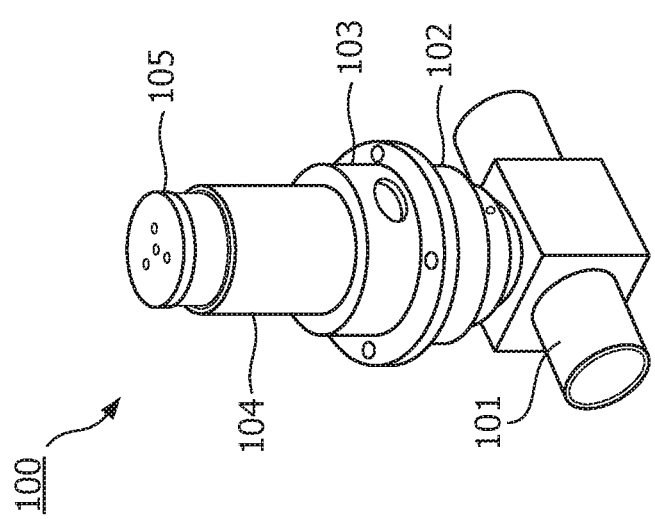

ACTIVE VALVE FOR VENTILATORS

This application is a divisional application of co-pending U.S. patent application Ser. No. 13/994,847, filed Jun. 17, 2013, which in turn claims the benefit of pending international application no. PCT/IB2011/055574, filed Dec. 9, 2011, which claims the benefit of U.S. provisional application Ser. No. 61/425,515, filed Dec. 21, 2010.

BACKGROUND

Ventilators are used in a variety of applications to provide non-invasive (e.g., via a mask) and invasive (e.g., via an endotracheal tube) ventilation of a patient.

A Safety Valve, Positive Pressure Relief Valve (PPRV) and Negative Pressure Relief Valve (NPRV) are components in a ventilator and are often required by standards applicable to ventilators. Normally in known ventilators, the safety valve, PPRV and NPRV are three separate parts and each provides a specific function. Notably, the safety valve ensures that the pressure in the patient circuit does not exceed a certain level; the PPRV allows for inhalation at a predetermined (positive) pressure; and the NPRV allows air from the ambient to be delivered to the patient when the negative pressure in the patient circuit exceeds a predetermined (negative) pressure (e.g., during ventilation system failure).

Known safety valves, PPRVs and NPRVs are normally purely mechanical in nature. As such, a threshold pressure is set (e.g., by a spring mechanism) and cannot be varied to accommodate different patient requirements during ventilation. For example, the safety valve can only be set to a specific value for relieving pressure above the highest pressure level in the ventilator, and the NPRV can be set to a specific negative pressure level for relieving pressure below a lowest pressure level in the ventilator. Additionally, over time in known actuators, the accuracy of the valve can be diminished.

What is needed is an apparatus and method for use in a ventilator that overcomes at least the shortcomings of the known apparatuses described above.

SUMMARY

In a representative embodiment, a valve for controlling a pressure in a ventilation system comprises: an electromagnet; a shaft connected to the electromagnet; and a diaphragm connected to the shaft. The electromagnet applies a force to the diaphragm based on an input.

In another representative embodiment, a ventilation system comprises a ventilator connected to a patient circuit; a valve configured to control a pressure in the ventilation system, the valve comprising: an electromagnet; a shaft connected to the electromagnet; and a diaphragm connected to the shaft. The ventilation system comprises a controller connected to the valve and configured to provide an input to the valve. The electromagnet applies a force to the diaphragm based on the input.

In accordance with another representative embodiment, a computer readable medium has a computer readable program code embodied therein. The computer readable program code is adapted to be executed to implement a method of controlling ventilation of a person. The method comprises: providing an inhalation pressure limit; determining when a pressure is greater than the inhalation pressure limit; and opening a valve when the pressure is greater than the inhalation pressure limit.

BRIEF DESCRIPTION OF THE DRAWINGS

The representative embodiments are best understood from the following detailed description when read with the accompanying drawing figures. The dimensions of features in the drawing figures may be arbitrarily increased or decreased for clarity of discussion. Wherever applicable and practical, like reference numerals refer to like elements.

FIG. 1A is perspective view of a valve in accordance with a representative embodiment.

FIG. 1B is an exploded view of the valve depicted in FIG. 1A.

DETAILED DESCRIPTION

Figure 2:
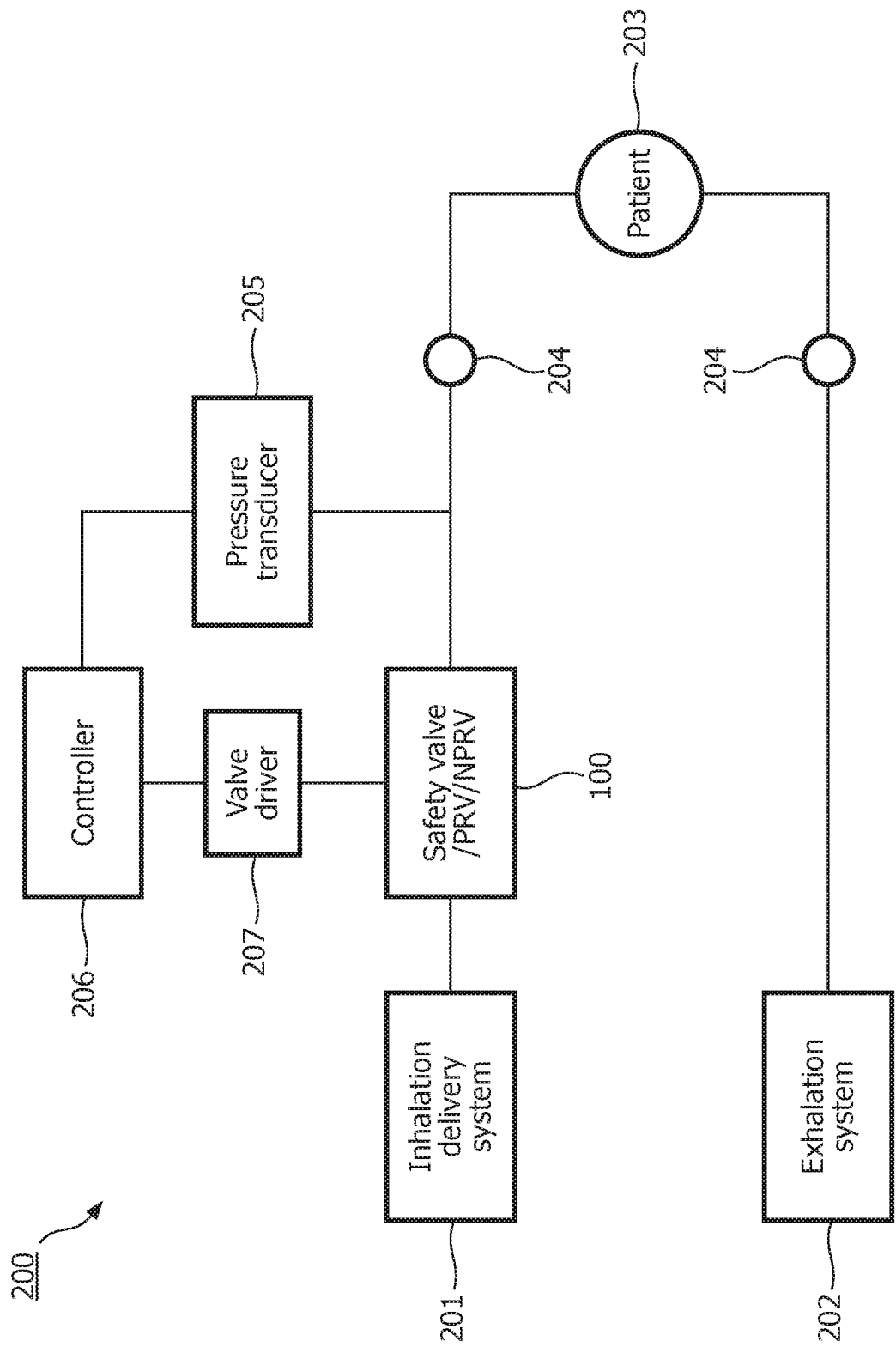
FIG. 2 is a simplified block diagram of a ventilation system in accordance with a representative embodiment.

In the following detailed description, for purposes of explanation and not limitation, representative embodiments disclosing specific details are set forth in order to provide a thorough understanding of embodiments according to the present teachings. However, it will be apparent to one having had the benefit of the present disclosure that other embodiments according to the present teachings that depart from the specific details disclosed herein remain within the scope of the appended claims. Moreover, descriptions of well-known devices and methods may be omitted so as not to obscure the description of the example embodiments. Such methods and devices are within the scope of the present teachings.

Unless otherwise noted, when a first device is said to be connected to a second device, this encompasses cases where one or more intermediate devices may be employed to connect the two devices to each other. However, when a first device is said to be directly connected to a second device, this encompasses only cases where the two devices are connected to each other without any intermediate or intervening devices.

In accordance with representative embodiments described below, a valve for use in a patient ventilation system is described. The valve functions as a safety valve, a PPRV and an NPRV and provides these functions as a single component. The valves of the representative embodiments are contemplated for use in non-invasive ventilation systems and in invasive ventilation systems.

FIG. 1A is perspective view of a valve 100 in accordance with a representative embodiment. The valve 100 is disposed over a connection 101 to a patient circuit (not shown in FIG. 1A), and provides pressure relief in ways described below in connection with representative embodiments. The valve 100 comprises a lower housing 102, which is affixed to the connection 101. An intermediate housing 103 is connected between the lower housing 102 and an upper housing 104. As described more fully below, the upper housing 104 contains an electromagnet, which comprises a coil 105.

FIG. 1B is an exploded view of the valve depicted in FIG. 1A. The coil 105 is disposed around a magnet 106. Together, the coil 105 and the magnet 106 comprise an electromagnet. A shaft 107 is attached to the coil 105 through magnet 106 and extends through the intermediate housing 103. The shaft 107 is connected to a plunger 109 via a connector 108 as shown. The plunger 109 is seated in a diaphragm 110 and the diaphragm 110 is seated over an opening (not shown) in the connection 101. As described more fully below, the coil 105 is driven in the positive and negative z-direction of the coordinate system shown in FIG. 1B by the application of current to the coil 105. The movement of the coil 105 results in movement of the shaft 107 in same z-direction, which in turn raises (+z-direction) or lowers (−z-direction) the plunger 109 and in turn raises (+z-direction) or lowers (−z-direction) the diaphragm 110.

The diaphragm 110 is illustratively made of rubber, or a polymer material, or other suitable material. The diaphragm 110 comprises sidewalls 111 that allow the diaphragm 110 to be raised and lowered in response to forces applied to the plunger 109 by the electromagnet. In accordance with representative embodiments, the electromagnet provides a force through the plunger 109 to the diaphragm 110 that is commensurate with a desired pressure in the connection 101 and, therefore, the patient circuit.

As described more fully below, the magnitude and direction (±z-direction) of the force provided by the diaphragm 110 is determined by the magnitude and direction of the current in the coil 105 determined by a controller (not shown in FIG. 1B). In certain embodiments, a threshold pressure is set in the controller. Based on feedback from a pressure transducer (not shown in FIG. 1B), the controller changes the direction of the current in the coil 105 to raise the plunger 109 and the diaphragm 110 via the shaft 107. The raising of the diaphragm 110 allows air to be released from the connection 101 to the ambient through an opening (not shown) in the lower housing 102, or allows air to be provided to the connection 101 from the ambient through the opening in the lower housing 102. In other embodiments, the diaphragm 110 is selectively raised and lowered to maintain the pressure in the patient circuit at a predetermined level set in the controller. The controller receives pressure data from the pressure transducer and raises the diaphragm 110 if the pressure in the patient circuit rises above the predetermined level, and lowers the diaphragm 110 if the pressure in the patient circuit falls below the predetermined level. The selective raising and lowering of the diaphragm 110 is in response to changes in the direction of current in the coil 105 based on signals from the controller.

Beneficially, when operating as a safety valve, based on the forces applied to the diaphragm 110, the valve 100 can be set to relieve positive pressure or negative pressure based on a positive pressure threshold or a negative pressure threshold, respectively, set in the controller. When operating as a pressure regulator, the valve 100 can maintain the pressure in the patient circuit at a predetermined level through the selective raising and lowering of the diaphragm 110 to provide pressure relief. The ability to set the positive and negative pressure thresholds and to regulate the pressure in the patient circuit allows for a single component, valve 100, to provide the functions of a safety valve, a PPRV, and a NPRV. Moreover, the ability to set the positive and negative pressure thresholds and to regulate the pressure in the patient circuit allows the valve 100 to be implemented in a variety of applications (e.g. neonatal ventilation, pediatric ventilation, and adult ventilation).

FIG. 2 is a simplified schematic diagram of a ventilator 200 in accordance with a representative embodiment. The ventilator 200 may be configured to provide non-invasive ventilation or invasive ventilation. The ventilator 200 comprises an inhalation delivery system 201 and an exhalation system 202, which are connected to a patient 203 via a patient circuit 204 comprising a patient interface (not shown). Certain aspects of the inhalation delivery system 201, the exhalation system 202, the patient circuit 204 and the patient interface of the ventilator 200 are known. For example, the inhalation delivery system 201, the exhalation system 202, the patient circuit 204 and the patient interface of the ventilator 200 of the ventilator 200 may be found, for example, in one of a variety of ventilators commercially available from Koninklijke Philips Electronics N. V., Eindhoven, The Netherlands.

The ventilator 200 comprises the valve 100 illustratively provided between the inhalation delivery system 201 and the patient 203. A pressure transducer 205 is connected to the patient circuit 204 between the patient 203 and the valve 100. The pressure transducer 205 provides an electrical signal indicative of the pressure (pressure readings) in the patient circuit 204 between the patient 203 and the valve 100. As described more fully below, these pressure readings are used to raise the diaphragm 110 (opening the valve 100), or to lower the diaphragm (closing the valve 100), or to maintain the diaphragm 110 in its current position.

The ventilator 200 comprises a controller 206, which receives the pressure readings from the pressure transducer 205, and provides commands to a valve driver 207. The valve driver 207 is illustratively a current amplifier/controller that provides a current in a particular direction and of a particular magnitude to the coil 105 of the valve 100 based on the commands from the controller 206. As described above, the magnitude and direction of the current through the coil 105 dictates the magnitude and direction of the force applied to the plunger 109 and thus to the diaphragm 110. As described more fully below, the movement of the diaphragm 110 and the force applied by the diaphragm 110 provide pressure relief or pressure regulation of the air in the patient circuit 204 between the patient 203 and the valve 100.

The controller 206 may be one of a variety of processing devices, such as a processor, microprocessor, or central processing unit (CPU), application specific integrated circuits (ASICs), field-programmable gate arrays (FPGAs), or combinations thereof, using software, firmware, hard-wired logic circuits, or combinations thereof. In a representative embodiment, the controller 206 is a controller (e.g., microprocessor) of the ventilator 200. In another embodiment, the controller 206 is a separate component from the ventilator 200. In such an embodiment, the controller 206, the pressure transducer 205 and the valve 100 comprise a stand-alone device that is connected to the patient circuit 204.

A memory (not shown) is included for storing executable software/firmware and/or executable code for the controller 206. The executable software/firmware and/or executable code enables the determination of the pressure in the patient circuit 204 between the valve 100 and the patient 203 based on the data received from the pressure transducer. The executable software/firmware and/or executable code enable the determination by the controller 206 of the required magnitude and direction of the current to be supplied by valve driver 207 to the coil 105 of the valve 100. The memory may be any number, type and combination of nonvolatile read only memory (ROM) and volatile random access memory (RAM), and may store various types of information, such as computer programs and software algorithms executable by the processor or CPU. The memory may include any number, type and combination of tangible computer readable storage media, such as a disk drive, an electrically programmable read-only memory (EPROM), an electrically erasable and programmable read only memory (EEPROM), a CD, a DVD, a universal serial bus (USB) drive, and the like.

As described above, the controller 206 provides commands to the valve driver 207 regarding the direction and magnitude of the current to be supplied to the coil based on pressure readings from the pressure transducer 205. In response, the valve 100 is configured to provide pressure relief or pressure regulation based on the pressure readings received from the pressure transducer 205. In one example, a threshold limit (positive or negative) is set for a pressure in the patient circuit 204. The threshold limit is the maximum (positive or negative) pressure that can safely be provided to the patient 203. Pressure values above the threshold limit could be dangerous to the patient. For example, if the pressure measured by the pressure transducer 205 exceeds the threshold limit, upon receiving these data from the pressure transducer 205, the controller 206 provides a command to the valve driver 207 to reverse the direction of current flow in the coil 105 of the valve 100. The reversal of current flow causes the diaphragm 110 to be raised (+z-direction in the coordinate system shown in FIG. 1B). If the threshold limit is a positive pressure, raising the diaphragm releases air to the ambient through the opening in the lower housing 102. In another embodiment, rather than reversing the direction of current flow, the current to the coil 105 from the valve driver 207 is terminated based on commands from the controller 206. With no current in the coil 105, no force is applied by the plunger 109 to the diaphragm 110. This results in the raising of the diaphragm 110 and the release of air to the ambient through the opening in the lower housing 102. As should be appreciated, in this example, the valve 100 functions as a safety valve.

In another example, a desired pressure in the patient circuit 204 between the patient 203 and the valve 100 is set in the controller 206. If the pressure reading received by the controller 206 from the pressure transducer 205 indicates that the pressure is greater than the desired pressure (but less than a positive threshold pressure), the controller 206 provides commands to the valve driver 207 to terminate current flow in the coil 105 or to reverse current flow in the coil 105 causing the diaphragm 110 to be raised (+z-direction in the coordinate system shown in FIG. 1B) and air to be released to the ambient through the opening in the lower housing 102. If the next measurement data from the pressure transducer 205 indicates that the pressure in the patient circuit 204 between the valve 100 and the patient 203 is at or below the desired pressure, the controller 206 provides commands to the valve driver 207 to provide current having a determined magnitude and direction to cause the diaphragm 110 to be lowered (−z-direction in the coordinate system shown in FIG. 1B) and to provide a suitable force at the opening (not shown) to maintain the seal between the diaphragm 110 and the opening in the connection 101. As described below in connection with a representative embodiment, the process of taking pressure readings and raising and lowering the diaphragm 110 as needed to regulate the pressure in the patient circuit 204 between the valve 100 and the patient 203 is iterative. As should be appreciated, in this example, the valve 100 functions as a positive pressure relief valve (PPRV).

In another example, a desired pressure in the patient circuit 204 between the patient 203 and the valve 100 is set in the controller 206. If the data received by the controller 206 from the pressure transducer 205 indicate that the pressure is a negative pressure (but not equal to a negative threshold pressure), the controller 206 provides commands to terminate current flow in the coil 105 or to reverse current flow in the coil 105 causing the diaphragm 110 to be raised (+z-direction in the coordinate system shown in FIG. 1B) and air to be provided to the patient circuit 204 from the ambient through the opening in the lower housing 102. If the next measurement data from the pressure transducer 205 indicates that the pressure in the patient circuit 204 between the valve 100 and the patient 203 is no longer at the negative pressure, the controller 206 provides commands to resume current flow to cause the diaphragm 110 to be lowered (−z-direction in the coordinate system shown in FIG. 1B) and to provide a force at the opening (not shown) sufficient to maintain the seal between the diaphragm 110 and the opening in the connection 101. As described below in connection with a representative embodiment, the process of taking pressure measurements and raising and lowering the diaphragm 110 as needed to regulate the pressure in the patient circuit 204 between the valve 100 and the patient 203 is iterative. As should be appreciated, in this example, the valve 100 functions as a negative pressure relief valve (NPRV).

By way of illustration of the use of valve 100 as an NPRV, consider the case where a patient 203 takes a "deep breath" with a magnitude so great that a blower (not shown) or other air source (not shown) in the inhalation delivery system 201 of the ventilator 200 could not provide a surge of air flow to the patient to satiate the breath required by the patient. In this case, the patient 203 will create a negative pressure to the patient circuit 204 between the patient 203 and the valve 100. This negative pressure is detected by the pressure transducer 205 and a pressure reading is provided to the controller 206. Based on the pressure reading, the controller 206 provides a command to the valve driver 207 to provide a current of magnitude and direction sufficient to raise the diaphragm and valve 100 will open to ambient through the opening in the lower housing 102. The pressure transducer 205 provides a subsequent pressure reading to the controller 206 and the pressure in the patient circuit 204 between the patient 203 and the valve 100 is maintained at the desired level through control of the diaphragm 110 of the valve 100.

Figure 3:
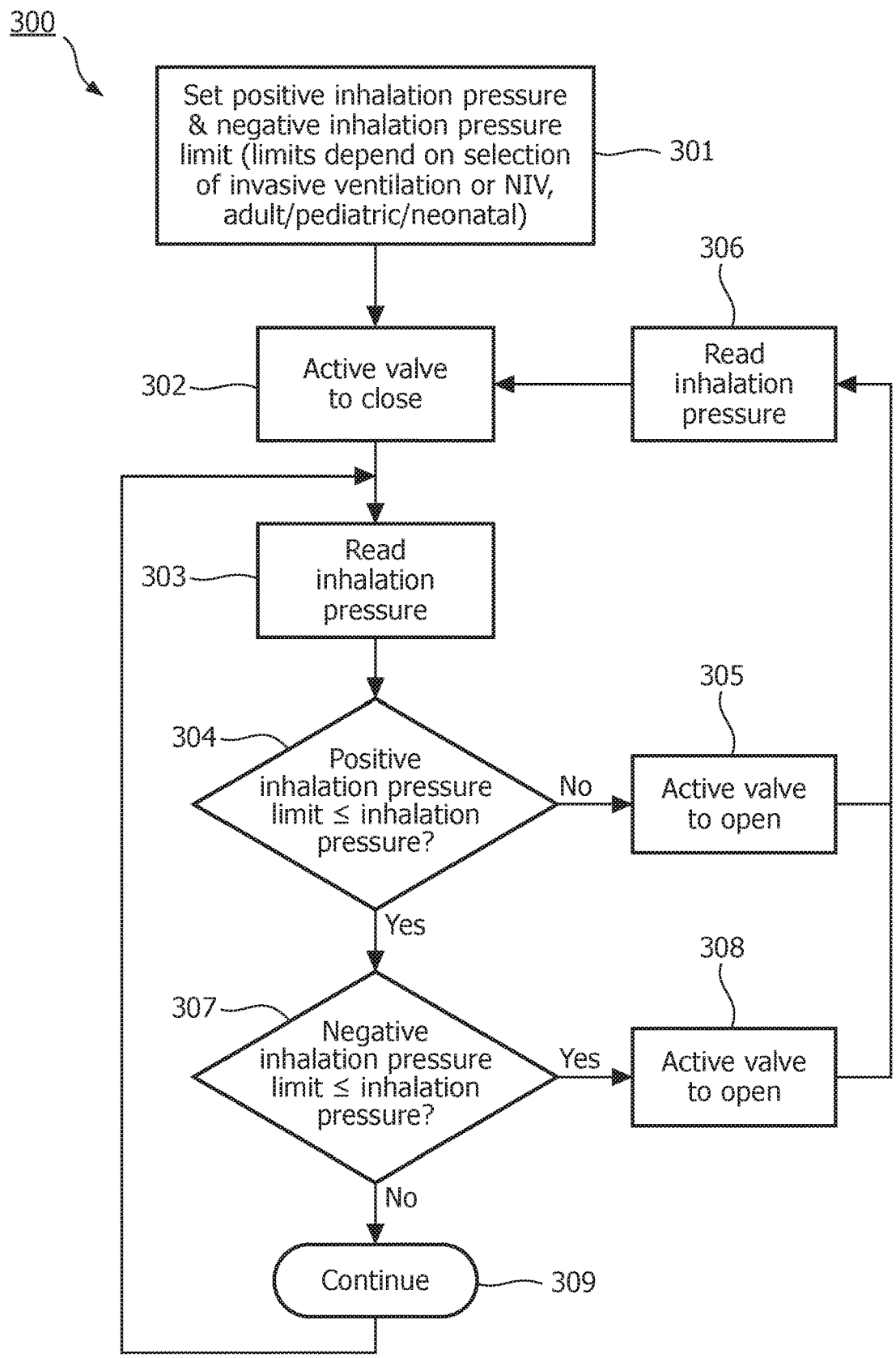
FIG. 3 is a flow diagram of a method of controlling a ventilation of a person in accordance with a representative embodiment.

FIG. 3 is a flow diagram of a method 300 of controlling a ventilation of a person in accordance with a representative embodiment. A computer readable medium having a computer readable program code embodied therein is stored in the memory accessible by the controller 206. The computer readable program code is adapted to be executed to implement the method through the controller 206.

At 301 the method comprises setting an inhalation pressure limit at the controller 206. In an embodiment where the valve 100 is functioning as a safety valve this inhalation pressure limit is either the positive pressure threshold for the patient circuit 204 between the valve 100 and the patient 203, or the negative pressure threshold for the patient circuit 204 between the valve 100 and the patient 203. As should be appreciated, both a positive pressure threshold and a negative pressure threshold can be set in the microprocessor. In embodiments where the valve 100 functions as a PPRV or as an NPRV, the inhalation pressure limit is the desired pressure in the patient circuit 204 between the patient 203 and the valve 100. It is emphasized that the valve 100 can be used as any of a safety valve, a PPRV and an NPRV. As such, the inhalation pressure limit can have multiple settings: the positive pressure threshold, the negative pressure threshold, and the desired pressure in the patient circuit 204 between the patient 203 and the valve 100. As should be appreciated, the positive and negative thresholds are significantly greater in magnitude than the desired pressure in the patient circuit 204 between the patient 203 and the valve 100.

Beneficially, the inhalation pressure limit may be adjusted for a particular application. For example, the inhalation pressure limit can be set at a value useful in neonatal ventilation. The inhalation pressure limit can be set at a value useful in pediatric ventilation that is a greater pressure limit (positive or negative) than the inhalation pressure limit useful in neonatal ventilation. Additionally, the inhalation pressure limit can be set at a value useful in adult ventilation that is a greater pressure limit (positive or negative) than the inhalation pressure limit useful in pediatric ventilation. Notably, these inhalation pressure limits are merely illustrative, and it is emphasized that a wide range of inhalation pressure limits can be provided at 301 to the controller 206.

At 302 the valve 100 is closed by lowering the diaphragm 110. As described above, current from the valve driver 207 is provided to the coil 105 and has a magnitude and direction determined by the controller 206 based on the desired pressure in the patient circuit 204 between the patient 203 and the valve 100.

At 303 an inhalation pressure is read. In a representative embodiment, a measurement of the pressure in the patient circuit 204 between the valve 100 and the patient 203 is made by the pressure transducer 205. This pressure reading is provided to the controller 206.

The controller 206 compares the pressure reading from the pressure transducer 205 to a positive inhalation pressure limit stored in the memory. If the positive inhalation pressure limit is less than or equal to the pressure reading by the pressure transducer 205, the method 300 continues at 305. At 305, the controller 206 provides a command to raise the diaphragm 110 of the valve 100. Raising the diaphragm 110 allows air to be released to the ambient through the opening in the lower housing 102.

At 306 another pressure measurement is made by the pressure transducer 205. The method 300 continues at 302 and the valve 100 is closed by lowering the diaphragm 110. As described above, the magnitude and direction of the current from the valve driver 207 is determined by the controller 206 based on the pressure readings at 306 to lower the diaphragm 110 and to ensure a suitable force is applied by the plunger 109 to the diaphragm 110 to maintain the diaphragm 110 in a closed position. When the inhalation limit is set to a desired positive pressure, the valve 100 functions as a PPRV.

The method 300 continues at 304. The controller 206 compares the pressure reading from the pressure transducer 205 to a positive inhalation pressure limit. If the positive inhalation pressure limit is greater than the pressure reading by the pressure transducer 205, the method 300 continues at 307.

At 307, the controller 206 compares the pressure reading from the pressure transducer 205 to a negative inhalation pressure limit stored in the memory. If the negative inhalation pressure limit is less than or equal to (in magnitude) the pressure reading by the pressure transducer 205, the method 300 continues at 308.

At 308, the controller 206 provides a command to raise the diaphragm 110 of the valve 100 to open the valve 100. Raising the diaphragm 110 allows for air from the ambient to be inhaled by the patient 203. As described above, the magnitude and direction of the current from the valve driver 207 is determined by the controller 206 based on the pressure readings at 307 to raise the diaphragm 110 with sufficient force to overcome the negative pressure in the patient circuit 204 between the patient 203 and the valve 100.

After the valve 100 is opened, the method 300 continues at 306 and another pressure measurement is made by the pressure transducer 205. The method 300 then continues at 302 and the valve 100 is closed by lowering the diaphragm 110. As described above, the magnitude and direction of the current from the valve driver 207 is determined by the controller 206 based on the pressure readings at 306 to lower the diaphragm 110 and to ensure a suitable force is applied by the plunger 109 to the diaphragm to maintain the diaphragm 110 in a closed position. When the inhalation limit is set to a desired positive pressure, the valve 100 functions as a PPRV.

If at 307 the negative inhalation pressure limit is greater (in magnitude) than pressure reading by the pressure transducer 205, the method 300 continues at 309 and the method 300 repeats beginning at 303 with the valve 100 closed. If the desired pressure is set between the positive inhalation pressure limit and the negative inhalation pressure limit, the repetition of the method 300 allows for the regulation of the pressure in the patient circuit 204 between the patient 203 and the valve 100.

In an embodiment, the positive inhalation pressure limit is set to the positive pressure threshold. If the pressure measured by the pressure transducer 205 is greater than the positive inhalation pressure limit, at 305 the diaphragm 110 is raised to release air to the ambient. In another embodiment, the negative pressure limit is set to the negative pressure threshold. If the pressure measured by the pressure transducer 205 is greater (in magnitude) than the negative inhalation pressure limit pressure limit, at 308 the diaphragm 110 is raised to receive air from the ambient. In embodiments where the positive inhalation pressure limit is set to the positive pressure threshold, or the negative inhalation pressure limit is set to the negative pressure threshold, the valve 100 functions as a safety valve. After functioning as a safety valve (at 305 or 308), the method 300 continues at 306 and repeats as described above.

While representative embodiments are disclosed herein, one of ordinary skill in the art appreciates that many variations that are in accordance with the present teachings are possible and remain within the scope of the appended claims. The invention therefore is not to be restricted except within the scope of the appended claims.

The invention claimed is:

1. A non-transitory computer readable medium having a computer readable program code embodied therein, the computer readable program code adapted to be executed to implement a method of controlling ventilation of a person, the method comprising:
   providing, via a controller, an inhalation pressure limit;
   determining, via a pressure sensor and the controller, when a pressure in a patient circuit coupled to a ventilation system is greater than the inhalation pressure limit; and
   opening a valve, via the controller, for controlling pressure and providing one or more of pressure relief and pressure maintenance, in the patient circuit coupled to the ventilation system when the pressure is greater than the inhalation pressure limit, wherein the valve comprises:
   an electromagnet;
   a shaft connected to the electromagnet; and
   a diaphragm connected to the shaft, wherein the electromagnet applies a force to the diaphragm via the shaft based on an input current signal, provided via the controller, to the electromagnet that dictates raising and lowering the diaphragm with respect to a connection to the patient circuit coupled to the ventilation system, wherein (a) raising the diaphragm (a)(i) enables air to be released in a controlled manner from the connection to an ambient through an opening in the valve in response to the input current signal based on a pressure in the patient circuit being greater than a desired pressure but less than the inhalation pressure limit, further in response to the inhalation pressure limit being a positive threshold pressure, and (a)(ii) allows air to be provided to the connection in a controlled manner from the ambient through the opening in the valve in response to the input current signal based on a negative pressure in the patient circuit being greater in magnitude than the inhalation pressure limit, further in response to the inhalation pressure limit being a negative pressure threshold, to function as a safety valve, and (b) lowering the diaphragm maintains a seal between the diaphragm and the opening in the valve in a controlled manner in response to the input current signal based on a pressure in the patient circuit being at or below a desired pressure.

2. The non-transitory computer readable medium as claimed in claim 1, wherein the method further comprises maintaining the valve in a closed position when the pressure is less than the inhalation pressure limit.

3. The non-transitory computer readable medium as claimed in claim 1, wherein the inhalation pressure limit is a positive pressure threshold.

4. The non-transitory computer readable medium as claimed in claim 1, wherein the inhalation pressure limit is a negative pressure threshold.

5. A method of controlling a valve for providing pressure relief and pressure regulation in a ventilation system, the method comprising:
   providing, via a controller, an inhalation pressure limit;
   determining, via a pressure sensor and the controller, when a pressure in a patient circuit coupled to the ventilation system is greater than the inhalation pressure limit; and
   opening the valve, via the controller, for controlling pressure and providing one or more of pressure relief and pressure regulation, in the patient circuit coupled to the ventilation system when the pressure is greater than the inhalation pressure limit, wherein the valve comprises:
an electromagnet;
a shaft connected to the electromagnet; and
a diaphragm connected to the shaft, wherein the electromagnet applies a force to the diaphragm via the shaft based on an input current signal, provided via the controller, to the electromagnet that dictates raising and lowering the diaphragm with respect to a connection to the patient circuit coupled to the ventilation system, wherein (a) raising the diaphragm (a)(i) enables air to be released in a controlled manner from the connection to an ambient through an opening in the valve in response to the input current signal based on a pressure in the patient circuit being greater than a desired pressure but less than the inhalation pressure limit, further in response to the inhalation pressure limit being a positive threshold pressure, and (a)(ii) allows air to be provided to the connection in a controlled manner from the ambient through the opening in the valve in response to the input current signal based on a negative pressure in the patient circuit being greater in magnitude than the inhalation pressure limit, further in response to the inhalation pressure limit being a negative pressure threshold, to function as a safety valve, and (b) lowering the diaphragm maintains a seal between the diaphragm and the opening in the valve in a controlled manner in response to the input current signal based on a pressure in the patient circuit being at or below a desired pressure.

6. The method as claimed in claim 5, further comprising: determining when the pressure is less than the inhalation pressure limit and maintaining the valve in a closed position when the pressure is less than the inhalation pressure limit.

7. The method as claimed in claim 5, wherein the inhalation pressure limit is a positive pressure threshold.

8. The method as claimed in claim 5, wherein the inhalation pressure limit is a negative pressure threshold.

* * * * *